(12) United States Patent
Patel

(10) Patent No.: US 7,670,618 B2
(45) Date of Patent: Mar. 2, 2010

(54) PHARMACEUTICAL COMPOSITIONS

(76) Inventor: Satishchandra P. Patel, 27 Yale St., Livingston, NJ (US) 07039

( * ) Notice: Subject to any disclaimer, the term of this patent is extended or adjusted under 35 U.S.C. 154(b) by 1669 days.

(21) Appl. No.: 10/632,970

(22) Filed: Aug. 4, 2003

(65) Prior Publication Data

US 2004/0048789 A1    Mar. 11, 2004

(30) Foreign Application Priority Data

Aug. 2, 2002    (GB) ................................ 0218002.4

(51) Int. Cl.
*A61K 9/48*    (2006.01)
*A61K 9/64*    (2006.01)
*A61K 9/66*    (2006.01)

(52) U.S. Cl. ........................ 424/451; 424/455; 424/456

(58) Field of Classification Search ........................ None
See application file for complete search history.

(56) References Cited

U.S. PATENT DOCUMENTS

| | | | |
|---|---|---|---|
| 4,388,307 A | 6/1983 | Cavanak | |
| 5,342,625 A | 8/1994 | Hauer et al. | |
| 5,645,856 A | 7/1997 | Lacy et al. | |
| 5,759,997 A | 6/1998 | Cavanak | |
| 5,858,401 A | 1/1999 | Bhalani et al. | |
| 6,057,289 A | 5/2000 | Mulye | |
| 6,294,192 B1 | 9/2001 | Patel et al. | |
| 6,436,430 B1 * | 8/2002 | Mulye | ........................ 424/439 |
| 2002/0009067 A1 | 1/2002 | Sachs et al. | |
| 2004/0110667 A1 * | 6/2004 | Linn | ........................... 514/11 |

FOREIGN PATENT DOCUMENTS

| | | |
|---|---|---|
| WO | WO 98/40051 | 9/1998 |
| WO | WO 00/33862 | 6/2000 |
| WO | WO 0033862 A1 * | 6/2000 |

\* cited by examiner

*Primary Examiner*—S. Tran
(74) *Attorney, Agent, or Firm*—Dickstein Shapiro LLP

(57) ABSTRACT

Discloses is a pharmaceutical composition suitable for oral administration in the form of a homogeneous solution which on exposure to water or gastrointestinal fluids forms an emulsion having a particle size of less than 5 microns, the solution containing:
(a) a pharmaceutically effective amount of a cyclosporin, in particular Cyclosporin A,
(b) a carrier medium which is a mixture of mono- and diesters of propylene glycol with fatty acids having from 8 to 10 carbon atoms or with mixtures of such fatty acids, wherein the monoester makes up less than 60 mol % of the mixture, and
(c) a non-ionic surfactant having a hydrophilic lipophilic balance (HLB) greater than 10.

18 Claims, No Drawings

PHARMACEUTICAL COMPOSITIONS

The present invention relates to pharmaceutical compositions, in particular a microemulsion concentrate for cyclosporins.

The cyclosporins are a class of cyclic undecapeptides, with important pharmacological activities, in particular immunosuppressive, anti-inflammatory and/or anti-parasitic activities. The first of the cyclosporins to be isolated, and the most commonly known cyclosporin, is Cyclosporin A, formulations of which are commercially available under the trade marks SANDIMMUNE and NEORAL.

The cyclosporins are very lipophilic and hydrophobic compounds, which are sparingly soluble in water, but dissolve readily in organic solvents such as methanol, ethanol, chloroform and the like. The low solubility in water results in extremely low bioavailability of the cyclosporins when administered orally. This may lead to higher dosages being required, with the consequent possibility of undesirable side effects. Therefore, to provide an effective therapeutic concentration of the drug in the body when administered orally represents a considerable challenge. Extensive research has been conducted to find cyclosporin formulations that are effective for oral administration. There are a number of preparations of cyclosporins suitable for oral administration proposed by the prior art.

Prior art formulations of cyclosporins for oral administration have often involved combinations of the cyclosporin with a surfactant, an oil, and a co-surfactant. Such formulations have been intended to be diluted with water prior to drinking. However, this is rather inconvenient, and also the resulting aqueous composition has an unpleasant taste.

In order to alleviate the problems of having to dilute the composition with water prior to oral administration, and the unpleasant taste of the resulting solution, liquid compositions have been formulated into soft capsule preparations. For example, the formulation commercially available under the trade mark SANDIMMUNE is encapsulated in a soft capsule with a gelatine shell. The formulation contains ethanol in order to solubilise the cyclosporin. However, the ethanol can permeate the gelatine shell of the capsule and is volatile at room temperature. This means that the composition of the contents can vary during storage. If too much ethanol is lost, the cyclosporin may precipitate from the composition, with adverse effects on the bioavailability. This results in uncertainties about dosage.

U.S. Pat. No. 4,388,307 discloses compositions comprising a cyclosporin together with at least one of the following components:
a) a trans-esterification product of a natural or hydrogenated vegetable oil triglyceride and a polyalkylene polyol;
b) a saturated fatty acid triglyceride; and
c) a mono- or di-glyceride.

It is preferred that ethanol be used as a further solubilising agent, and the compositions for oral administration disclosed in the Examples all contain ethanol.

U.S. Pat. No. 5,342,625 discloses pharmaceutical compositions comprising cyclosporins in microemulsion pre-concentrate and micro-emulsion form. The compositions contain a cyclosporin disposed in a composition comprising a hydrophilic phase, a lipophilic phase and a surfactant. The hydrophilic phase comprises 1,2-propylene glycol or $R_1$—(O—$(CH_2)_x$—$OR_2$ wherein $R_1$ is a $C_{1-5}$ alkyl or a tetrahydrofurfuryl group, $R_2$ is a $C_{1-5}$ alkyl or a tetrahydrofurfuryl group or is hydrogen, and X is from 1 to 6. The lipophilic phase typically comprises a fatty acid triglyceride. The compositions may contain a $C_{1-5}$ alkanol, such as ethanol, as a co-solvent. However, the compositions disclosed in U.S. Pat. No. 5,342,625 include components which are restricted for pharmaceutical use by several regulatory agencies world-wide, including the FDA, because they are not considered "Generally Recognised As Safe" (GRAS) for oral use.

U.S. Pat. No. 5,759,997 discloses pharmaceutical compositions comprising a cyclosporin, a fatty acid triglyceride, and a glycerol fatty acid partial ester or propylene glycol or sorbitol complete or partial ester. The compositions may also comprise a viscosity reducer, such as the trans-sterification product of a natural vegetable oil triglyceride and a polyalkylene polyol. Ethanol can also be used, but is less preferred. The compositions may also comprise an emulsifying agent, preferably a tenside having a hydrophilic-lipophilic balance (HLB) of at least 10.

U.S. Pat. No. 6,057,289 discloses pharmaceutical compositions comprising cyclosporin and a carrier comprising
(a) a cyclosporin solubilising agent consisting essentially of $C_6$ to $C_{22}$ fatty acids; and
(b) a water-soluble non-ionic surfactant.

The surfactant should have a hydrophilic-lipophilic balance (HLB) greater than 10, and suitable surfactants include polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives and the like. The compositions are for forming microemulsions upon contact with an aqueous medium.

U.S. Pat. No. 5,858,401 discloses compositions that comprise a cyclosporin, a medium chain monoglyceride of $C_6$ to $C_{12}$ fatty acids, having a monoglyceride content of at least 50%, and at least one surfactant. The surfactant may be, for example, polyglycolised glycerides or ethoxylated glycerides having a molecular weight of PEG between 400 and 2000 and a fatty acid chain length between $C_6$ to $C_{18}$. The compositions are for forming microemulsions upon contact with an aqueous medium.

WO 00/33862 discloses cyclosporin formulations comprising propylene glycol monoesters of $C_6$-$C_{18}$ fatty acids. The monoester content employed is typically >90%, and usually 100%. Comparative Example 2 of this publication shows that when propyleneglycol laurate with a monoester content of 45-50% is used, the cyclosporin is not solubilised and precipitation and crystal growth occurs after two weeks.

Having regard to the state of the art, it is clear that it is desirable to provide further formulations of cyclosporins suitable for oral administration, and in particular ones which can be formulated in capsules such as soft gelatine capsules, and which are emulsion concentrates (that is, homogeneous solutions which on exposure to water or gastrointestinal fluids form an emulsion having a particle size of less than 5 microns), and preferably microemulsion concentrates, which avoid the use of volatile components such as ethanol, and which utilise compounds which are Generally Recognised As Safe (GRAS).

Another problem in formulating cyclosporin is the potential hygroscopicity of the formulations. It is clearly important to the stability of the formulation to reduce absorption of water by the formulation. However, this is particularly important in the case when the delivery form is a soft gel capsule, because if water is absorbed from the shell of the soft gel capsule then the shell becomes brittle.

There is also a continued need to provide cyclosporin formulations for oral administration which can have high cyclosporin concentrations (thereby reducing the size of capsule required for a given dosage), which exhibit high oral bioavailability, and which are stable (in particular stable against precipitation of the cyclosporin) upon storage. It is also desirable that formulations should have as few components as possible, thereby resulting in ease of manufacture.

The present invention aims to provide cyclosporin compositions which, at least to some extent, satisfy these requirements.

According to the present invention, there is provided a pharmaceutical composition suitable for oral administration in the form of a homogeneous solution which on exposure to water or gastrointestinal fluids forms an emulsion having a particle size of less than 5 microns, the solution comprising:
(a) a pharmaceutically effective amount of a cyclosporin,
(b) a carrier medium comprising a mixture of mono- and diesters of propylene glycol with fatty acids having from 8 to 10 carbon atoms or with mixtures of such fatty acids, wherein the monoester makes up less than 60 mol % of the mixture, and
(c) a non-ionic surfactant having a hydrophilic lipophilic balance (HLB) greater than 10.

The present invention is partly based upon the discovery that the carrier medium as defined in (b) above represents a particularly good solvent medium for cyclosporins, and therefore it is possible to avoid co-solvents such as ethanol, propylene glycol, or the like. The compositions according to the present invention accordingly preferably do not have such co-solvents, and in particular preferably do not contain ethanol.

Surprisingly, having regard to the teaching of WO 00/33862, according to the present invention it has been found that, provided a $C_8$ to $C_{10}$ fatty acid is used, then effective solubilisation of cyclosporin can be obtained when less than 60%, preferably between 50 and 60%, monoester content is employed. Thus, according to the present invention, the combination of the correct fatty acid and the correct monoester content that allow effective solubilisation of cyclosporin. Furthermore, reducing the monoester content reduces the hygroscopicity of the formulation.

The compositions according to the present invention preferably do not contain appreciable amounts of water, that is, they are substantially water-free.

The compositions according to the present invention exhibit excellent stability upon storage, and high concentrations of cyclosporins in the compositions can be achieved.

The compositions according to the present invention are homogeneous mixtures which exhibit excellent bioavailability of the cyclosporin in vivo.

The cyclosporin is preferably Cyclosporin A. The cyclosporin preferably makes up from 1 to 25% by weight of the composition, more preferably makes up from 5 to 20% by weight of the composition, even more preferably makes up from 10 to 20% by weight of the composition, and most preferably makes up from 15 to 20% by weight of the composition. The cyclosporin is present in the composition of the present invention in pharmaceutically effective amounts. These amounts are well-known in the art. For example, when treating chronic inflammations or provoking an immunosuppressive effect, it is preferred that the daily dose ranges from about 3 mg/kg to about 50 mg/kg.

The carrier medium preferably makes up from 20 to 80% by weight of the composition, more preferably makes up from 35 to 60% by weight of the composition, and most preferably makes up from 40 to 55% by weight of the composition. In the carrier medium, the monoester preferably makes up between 50 and 60 mol % of the mixture of mono- and diesters.

In a particularly preferred embodiment, the carrier medium consists of a mixture of mono- and diesters of propylene glycol with capric and caprylic acids. In another particularly preferred embodiment, the carrier medium consists of a mixture of mono- and diesters of propylene glycol with caprylic acid. Suitable products are available commercially as IMWITOR 408 and CAPRYOL PGMC.

The non-ionic surfactant preferably makes up from 5 to 60% by weight of the composition, more preferably makes up from 20 to 50% by weight of the composition, and most preferably makes up from 30 to 40% by weight of the composition.

The Hydrophilic Lipophilic Balance (HLB) of the non-ionic surfactant is greater than 10, more preferably greater than 12 and most preferably greater than 14.

The non-ionic surfactant must be capable of forming a stable emulsion, preferably a fine emulsion (particle size less than 1 micron), and more preferably a microemulsion, of the composition when it is brought into contact with aqueous fluid, such as in the G.I. tract.

The non-ionic surfactant is preferably selected from the group consisting of: polyoxyethylene products of hydrogenated vegetable oils, polyethoxylated castor oils, polyethoxylated hydrogenated castor oil, polyoxyethylene-sorbitan-fatty acid esters, and polyoxyethylene castor oil derivatives. Particularly preferred surfactants are set out in Table 1. Mixtures of these surfactants can also be used.

TABLE 1

| Trade Name | Description |
|---|---|
| TWEEN 20 | Polyoxyethylene (20) sorbitan monolaurate |
| TWEEN 40 | Polyoxyethylene (20) sorbitan monopalmitate |
| TWEEN 60 | Polyoxyethylene (20) sorbitan monostearate |
| TWEEN 80 | Polyoxyethylene (20) sorbitan monooleate |
| NIKKOL HCO30 | PEG-30 hydrogenated castor oil |
| NIKKOL HCO40 | PEG-40 hydrogenated castor oil |
| NIKKOL HCO50 | PEG-50 hydrogenated castor oil |
| NIKKOL HCO60 | PEG-60 hydrogenated castor oil |
| CREMOPHORE RH40 | Polyoxyethylene 40 castor oil |
| CREMOPHORE RH60 | Polyoxyethylene 60 castor oil |
| CREMOPHORE EL35 | Polyoxyethylene 35 castor oil |

The pharmaceutical compositions according to the present invention may further comprise an antioxidant. This antioxidant, when present, is preferably present in an amount of from 0.01% to 2% by weight of the composition, and more preferably from 0.5 to 1% by weight of the composition. The antioxidant may be any suitable antioxidant, such as are well known to those skilled in the art. Particularly preferred antioxidants are butyl hydroxy anisole (BHA), butyl hydroxy toluene (BHT), and alpha-tocopherol.

Other additives, excipients, and diluents normally used in the pharmaceutical arts may optionally be added to the composition. These include thickening agents, dispersing agents, flavouring agents, sweetening agents, colouring agents, stabilising agents (including pH stabilisers), and preservatives. However, the compositions of the present invention preferably consist only of the cyclosporin, carrier medium, and a non-ionic surfactant, or at least comprise at least 90%, more preferably at least 95%, and more preferably at least 98% by weight of such components.

The pharmaceutical compositions according to the present invention may be formulated as a drinking solution, or as a hard or soft capsule. Soft capsule formulations are particularly preferred. Gelatine capsules are also preferred.

The pharmaceutical compositions according to the present invention can be conveniently prepared by uniformly and thoroughly mixing the carrier medium, the cyclosporin, and the surfactant together at room temperature or at slightly elevated temperature, such as a temperature up to 40° C., until a clear solution is obtained, and then cooling the composition to room temperature. The other additives indicated above are then thoroughly admixed therewith. The cyclosporin remains in solution and does not crystallise or precipitate out.

Compositions according to the present invention are preferably for administration to mammals, and especially to humans. It is preferred that the pharmaceutical compositions of the present invention are administered in capsule, liquid-oral, drink solution, or the like form. In a preferred embodiment, the composition is in a form adapted for oral administration in oral unit dosage form. Capsules, e.g., soft or hard gelatine capsules, which represent the preferred oral dosage form, are specially suitable unit dosage forms for oral administration.

Oral unit dosage forms in accordance with the present invention will suitably comprise from 5 to 400 mg and more preferably from 20 to 200 mg, e.g., 25, 50, 100, 125, 150, or 200 mg of cyclosporin. The dosage of the drug and the number of times administered to the patient will vary depending on several factors such as: the age of the patient, the severity of the condition of the patient, and past medical history, and will be a matter to be determined by the attending physician.

When the composition of the present invention is prepared in the form of a soft or hard capsule, the composition may be encapsulated in a gelatine shell which contains any conventional plasticizer. Suitable plasticizers are: glycerine, sorbitol, hexanetriol propylene carbonate, hexane glycol, sorbitans, tetrahydrofuryl alcohol ether, diethylene glycol monoethyl ether, 1,3-trimethyl-2-imidazolidone, dimethylisosorbide, and mixtures of these. However, the plasticizer is not limited to those just mentioned, and any suitable plasticizer can be used.

Encapsulation can be achieved by standard techniques which are well known in the art.

Compositions according to the present invention exhibit high solubility of cyclosporin, thereby reducing the size of the capsule or other oral unit dosage form. They also employ only materials that are GRAS for oral use.

The invention will now be further described with reference to the following Examples, it being understood that these are intended to illustrate the invention, and in no way to limit its scope.

EXAMPLES

The examples used the ingredients and in the amounts indicated in Table 2. Cyclosporin A was dissolved in the carrier medium, the surfactant was added, and the mixture was mixed for from 10 to 30 minutes at room temperature until the solution was homogeneous.

The solution was then stored overnight up to 24 hours to ensure that no crystallisation occurred.

TABLE 2

| Ingredients | Example 1 Weight/mg | Example 2 weight/mg | Example 3 weight/mg | Example 4 weight/mg |
|---|---|---|---|---|
| Cyclosporin A | 100 | 25 | 100 | 100 |
| Mono/diester of propylene glycol with caprylic acid (IMWITOR 408) | 285 | 100 | 285 | 170 |
| Mono/diester of propylene glycol with caprylic acid (CAPRYOL PGMC) | | | | 130 |
| Polyoxyethylene 35 castor oil (CREMOPHORE EL35) | 195 | | 195 | 180 |
| Polyoxyethylene 20 sorbitan monolaurate (TWEEN 20) | | 80 | | |
| Alpha tocopherol | | | 5 | |
| TOTAL | 580 mg | 205 mg | 585 mg | 580 mg |

To verify that an emulsion was formed, one part of each composition was added to 10 parts of water and stirred gently. There was formed a fine emulsion having a particle size of less than 5 microns, and the Cyclosporin A did not precipitate or crystallise out.

The compositions are suitable for encapsulation into a hard or soft gelatine capsule.

COMPARATIVE EXAMPLES

The formulation of Example 1 was compared with analogous examples in which the carrier medium was a diester of propylene glycol with capric/caprylic acids (MIGLYOL 840) (Comparative Example 1); a mixture of mono- and diesters of propylene glycol with lauric acid (LAUROGLYCOL FCC) (Comparative Example 2); and a mixture of mono and diglycerides of capric/caprylic acids (CAPMUL MCM) (Comparative Example 3).

The compositions were prepared by mixing the components set out in Table 3 at room temperature until a clear solution was formed. The resulting solutions were maintained at room temperature for four weeks and then compared. The results are shown in Table 4.

TABLE 3

| Ingredients | Example 1 weight/mg | Comparative Example 1 weight/mg | Comparative Example 2 weight/mg | Comparative Example 3 weight/mg |
|---|---|---|---|---|
| Cyclosporin A | 100 | 100 | 100 | 100 |
| Mono/diester of propylene glycol with caprylic acid (IMWITOR 408) | 285 | | | |
| Diester of propylene glycol with capric/caprylic acids (MIGLYOL 840) | | 285 | | |
| Mono/diester of propylene glycol with lauric acid (LAUROGLYCOL FCC) | | | 285 | |
| Mono/di-glycerides of capric/caprylic acids (CAPMUL MCM) | | | | 285 |
| Polyoxyethylene 35 castor oil (CREMOPHORE EL35) | 195 | 195 | 195 | 195 |
| Alpha tocopherol | 5 | 5 | 5 | 5 |
| TOTAL | 585 mg | 585 mg | 585 mg | 585 mg |

TABLE 4

| Conditions | Example 1 | Comparative Example 1 | Comparative Example 2 | Comparative Example 3 |
|---|---|---|---|---|
| | | Observation | | |
| Initial | Clear solution | Hazy solution | Clear solution | Clear solution |
| 4 weeks at 25° C. | Clear solution | Precipitation hazy solution | Hazy solution | Hazy solution |
| 4 weeks at 40° C. + 75% RH | Clear solution | Precipitation hazy solution | Hazy solution | Hazy solution |

Hygroscopicity Test

Hygroscopicity tests show that whereas propyleneglycol ester of $C_8$ fatty acid with monoester content about 90% (see Example 8 of WO 00/33862) absorbs 3-4% of moisture from a soft gel capsule, a propyleneglycol ester of $C_8$ fatty acid with monoester content of between 50 and 60%, as used in the present invention, absorbs only 1-2% moisture.

The invention claimed is:

1. A pharmaceutical composition suitable for oral administration in the form of a homogeneous solution which on exposure to water or gastrointestinal fluids forms an emulsion having a particle size of less than 5 microns, the solution comprising: (a) a pharmaceutically effective amount of a cyclosporin, (b) a carrier medium comprising a mixture of mono- and diesters of propylene glycol with fatty acids having from 8 to 10 carbon atoms or with mixtures of such fatty acids, wherein the monoester makes up between 50 and 60 mol % of the mixture, and (c) a non-ionic surf actant having a hydrophilic lipophilic balance (HLB) greater than 10.

2. A pharmaceutical composition according to claim 1, wherein the cyclosporin is 5 to 20% by weight of the composition, the carrier medium is 35 to 60% by weight of the composition, and the non-ionic surfactant is 20 to 50% by weight of the composition.

3. A pharmaceutical composition according to claim 1, wherein the cyclosporin is 15 to 20% by weight of the composition, the carrier medium is 40 to 55% by weight of the composition, and the non-ionic surfactant is 30 to 40% by weight of the composition.

4. A pharmaceutical composition according to claim 1, wherein said carrier medium consists of a mixture of mono- and diesters of propylene glycol with capric and caprylic acids.

5. A pharmaceutical composition according to claim 1, wherein said carrier medium consists of a mixture of mono- and diesters of propylene glycol with caprylic acid.

6. A pharmaceutical composition according to claim 1, wherein the cyclosporin is 1 to 25% by weight of the composition, the carrier medium is 20 to 80% by weight of the composition, and the non-ionic surfactant is 5 to 60% by weight of the composition.

7. A pharmaceutical composition according to claim 1, wherein the non-ionic surfactant is selected from the group consisting of: polyoxyethyled products of hydrogenated vegetable oil, polyethoxylated castor oil, polyethoxylated hydrogenated castor oil, polyoxyethylene-sorbitan-fatty acid ester, polyoxyethylene castor oil derivative, and mixtures thereof.

8. A pharmaceutical composition, according to claim 7, wherein the non-ionic surf actant is selected from the group consisting of polyoxyethylene (20) sorbitan monolaurate, polyoxyethylene (20) sorbitan monopalmitate, polyoxyethylene (20) sorbitan monostearate, polyoxyethylene (20) sorbitan monooleate, PEG-30 hydrogenated castor oil, PEG-40 hydrogenated castor oil, PEG-SO hydrogenated castor oil, PEG-60 hydrogenated castor oil, polyoxyethylene 40 castor oil, polyoxyethylene 60 castor oil, polyoxyethylene 35 castor oil, and mixtures thereof.

9. A pharmaceutical composition according to claim 1, further comprising an antioxidant.

10. A pharmaceutical composition according to claim 9, wherein the antioxidant is selected from the group consisting of BHA, BHT, and alpha-tocopherol.

11. A pharmaceutical composition according to claim 1, wherein the cyclosporin is Cyclosporin A.

12. A pharmaceutical composition according to claim 1, wherein the cyclosporin is 5 to 400 mg and is 1 to 25% by weight of the composition, the carrier medium is 20 to 80% by weight of the composition and is a mixture of mono- and diesters of propylene glycol with capric and caprylic acids or a mixture of mono- and diesters of propylene glycol with capric and caprylic acids in which the monoester is between 50 and 60 mol % of the mixture of mono- and diesters, the non-ionic surfactant is 5 to 60% by weight of the composition and has a HLB greater than 12, and the composition contains antioxidant in an amount of from 0.01% to 2% by weight of the composition.

13. A pharmaceutical composition according to claim 1, wherein the cyclosporin is 20 to 200 mg of Cyclosporin A and is 15 to 20% by weight of the composition, the carrier medium is 40 to 55% by weight of the composition and is a mixture of mono- and diesters of propylene glycol with capric and caprylic acids or a mixture of mono- and diesters of propylene glycol with capric and caprylic acids in which the monoester is between 50 and 60 mol % of the mixture of mono-and diesters, the non-ionic surfactant is 30 to 40% by weight of the composition and has a HLB greater than 14, and the composition contains antioxidant in an amount of from 0.5% to 1% by weight of the composition.

14. A pharmaceutical composition according to claim 13, formulated as a drinking solution.

15. A pharmaceutical composition according to claim 1, formulated as a drinking solution.

16. A pharmaceutical composition according to claim 1 formulated as a hard or soft capsule.

17. A pharmaceutical composition according to claim 14 contained within a soft gelatine capsule.

18. A pharmaceutical composition according to claim 1 contained within a soft gelatine capsule.

* * * * *